(12) United States Patent
Cary et al.

(10) Patent No.: US 7,361,477 B2
(45) Date of Patent: Apr. 22, 2008

(54) METHODS AND COMPOSITIONS FOR INHIBITING CELLULOLYTIC SYMBIONTS

(75) Inventors: Stephen C. Cary, Lewes, DE (US); Alison R. Sipe McDonald, Arlington, VA (US)

(73) Assignee: University of Delaware, Newark, DE (US)

( * ) Notice: Subject to any disclaimer, the term of this patent is extended or adjusted under 35 U.S.C. 154(b) by 386 days.

(21) Appl. No.: 10/474,621

(22) PCT Filed: Apr. 9, 2002

(86) PCT No.: PCT/US02/10928

§ 371 (c)(1),
(2), (4) Date: Jun. 24, 2004

(87) PCT Pub. No.: WO02/083381

PCT Pub. Date: Oct. 24, 2002

(65) Prior Publication Data

US 2004/0241091 A1    Dec. 2, 2004

Related U.S. Application Data

(60) Provisional application No. 60/282,962, filed on Apr. 11, 2001.

(51) Int. Cl.
    *G01N 33/53* (2006.01)
(52) U.S. Cl. ....................................... 435/7.2
(58) Field of Classification Search ..................... None
     See application file for complete search history.

(56) References Cited

U.S. PATENT DOCUMENTS 4,504,468 A    3/1985    Brill et al.

OTHER PUBLICATIONS

Sandermann et al., Occurrence of tryptamine in wood (Dicorynia guianesis), Naturwissenchaften, 1967, vol. 54, No. 10, p. 249 (Abstract).

Imam et al., Adhesive Properties of a Symbiotic Bacterium from a Wood-Boring Marine Shipworm, Applied and Environmental Microbiology, May 1990, vol. 56, No. 5, pp. 1317-1322.

Sipe et al., Bacterial Symbiont Transmission in the Wood-Boring Shipworm *Bankia setacea* (Bivalvia: Teredinidae), Applied and Environmental Microbiology, Apr. 2000, vol. 66, No. 4, pp. 1685-1691.

Alison R. Sipe et al., "Bacterial Symbiont Transmission in the Wood-Boring Shipworm *Bankia setacea* (Bivalvia: Teredinidae)," *Applied and Environmental Microbiology*, Apr. 2000, pp. 1685-1691, vol. 66, No. 4.

Waterbury, John B.; Calloway, C. Bradford; Turner, Ruth D.; "A Cellulolytic Nitrogen-Fixing Bacterium Cultured from the Gland of Deshayes in Shipoworms (*Bivalvia: Teredinidae*)"; Science, Sep. 30, 1983, vol. 221; pp. 1401-1403.

*Primary Examiner*—Ralph Gitomer
*Assistant Examiner*—Bin Shen
(74) *Attorney, Agent, or Firm*—RatnerPrestia

(57) ABSTRACT

Shipworms are important destroyers of wood in the marine environment. Wood users have long sought methods for preventing or limiting their attack. The invention is directed to compositions and methods for preventing or limiting cellulolytic degradation by inhibiting cellulolytic organisms, in particular symbiont organisms. The invention discloses methods and compositions to inhibit the growth of a shipworm symbiont responsible for wood degradation.

5 Claims, No Drawings

METHODS AND COMPOSITIONS FOR INHIBITING CELLULOLYTIC SYMBIONTS

This application claims priority to application Ser. No. 60/282,962, filed Apr. 11, 2001, the disclosure of which is incorporated herein by reference in its entirety.

The work to develop the invention was supported through a grant from the National Oceanic and Atmospheric Administration. The U.S. government may have certain rights in the invention.

FIELD OF THE INVENTION

The invention relates to compositions and methods of wood preservation in terrestrial and aquatic environments. Moreover, the invention relates to methods for screening compositions that may be useful for wood preservation, and to compositions identified thereby.

BACKGROUND OF THE INVENTION

The protection of wood exposed in aquatic and terrestrial environments has long posed a challenge. For centuries, marine borers were a major cause of deterioration of wooden ships and the economic well being of seafaring nations depended upon their ability to maintain a sea-worthy fleet. While wooden ships no longer play a major role in maritime commerce, wood forms an important component of the marine infrastructure, particularly in underdeveloped countries. In the developed countries, wooden ships, pilings, and buildings are important components of authentic reconstruction of historical towns and fishing villages. Wood used in these exposures is typically treated with high levels of preservatives that can include creosote, chromated copper arsenate, or ammoniacal copper zinc arsenate. While these chemicals are very effective, concerns have arisen about the potential for their migration into the surrounding water column and the effect on non-target marine organisms. There remains a public demand for the development of less toxic marine wood treatments.

Similarly, degradation of wood in terrestrial environments by the action of termites and other insects has been met by use of lumber pressure treated with many of the above agents, including arsenates. Contamination of soils and fresh water supplies from leaching from pressure treated lumber is an environmental concern.

One problem with developing alternative treatments is a lack of knowledge about how the current treatments affect various marine borers and terrestrial insects. This lack of knowledge stems from the widespread effectiveness of the chemicals currently used for this purpose, which has up to now suppressed development of commercially economic, environmentally safer alternatives. Aquatic wood protection, and wood protection in general, has tended to develop by increasing the amount of preservative to achieve a toxic threshold, then further increasing the preservative or treatment to ensure that most of the treated wood achieves this level of protection. This approach results in little concern for the effects of the toxicant on the target organism. Applicants found that the development of alternative control strategies for marine environments can be accomplished by a more intimate knowledge of marine borer biology.

Teredinid bivalves (shipworms) are important degraders of wood in marine environments. Unlike other marine wood borers, shipworms use wood as a food source, but they do so via symbiotic cellulolytic nitrogen fixing bacteria. Waterbury, et al. *A cellulolytic nitrogen-fixing bacterium cultured from the Gland of De shayes in shipworms*(Bivalvia: Tereinidae), 221 Science 1401 (1983). The role of these bacteria in shipworm biology, particularly as it relates to substrate selection, remains poorly understood. Similarly, termites use a flagellated protozoan (genus *Trichonympha*) as symbiont.

The invention discloses tests to identify inhibitors of a symbiont cellulolytic organism and to identify new compounds for wood treatment to limit or prevent degradation, preferably compounds that have fewer environmental problems that those presently used.

SUMMARY OF THE INVENTION

The invention is directed generally to methods for identifying compositions useful for inhibiting wood degradation, and to the compositions identified by the methods.

In one aspect, the invention is directed to a method for identifying a composition for limiting or preventing shipworm damage comprising the steps of: (a) incubating a shipworm symbiont in the absence and presence of a test composition under conditions such that the shipworm symbiont grows, has metabolic function, or both, in the absence of the test composition and (b) comparing the growth, metabolic function, or both, in shipworm symbionts in the absence and presence of the test composition; wherein if the growth, metabolic function, or both, in shipworm symbionts is less in the presence of the test composition than in the absence of the test composition, the test composition is a composition for limiting or preventing shipworm damage. In one aspect the conditions are limited to measurement and comparison of the growth of the shipworm symbiont. In one aspect the viability of the symbiont is measured and compared. In a preferred aspect, the invention is directed to a method wherein the symbiont is a *Teredinibacter*. In a preferred aspect, the invention is directed to a method wherein the test composition is a wood extract. In a more preferred aspect, the invention is directed to a method wherein the wood extract is an aqueous extract from a wood selected from the group consisting of Douglas-fir, ebony, jarrah, koa, lignum vitae, narra, Osage orange, paducah, purpleheart, red alder, red oak, teak, verawood, and western redcedar. In a yet more preferred aspect, the invention is directed to a method wherein the wood is selected from the group consisting of jarra, koa, red oak, and western redcedar. In a still more preferred embodiment, the wood extracts have been analyzed and specific compounds within the extract have been identified that function to inhibit or prevent wood degradation.

In one aspect, the invention is directed to a composition identified by a method comprising the steps of: (a) incubating a shipworm symbiont in the absence and presence of a test composition under conditions such that the shipworm symbiont grows, has metabolic function, or both, in the absence of the test composition and (b) comparing the growth, metabolic function, or both, in shipworm symbionts in the absence and presence of the test composition; wherein if the growth, metabolic function, or both, in shipworm symbionts is less in the presence of the test composition than in the absence of the test composition, the test composition is a composition for limiting or preventing shipworm damage. In a preferred aspect, the composition does not consist essentially of a copper-containing compound, a chromium-containing compound, an arsenic-containing compound, creosote, or combinations thereof. In one aspect, the invention is directed to a method of wood preservation comprising treating the wood with a composition identified by the above assay method.

In another aspect, the invention is directed to a method for identifying a composition for inhibiting growth, metabolic function, or both, of a cellulolytic organism capable of existing as a symbiont comprising the steps of: (a) incubating a cellulolytic organism capable of existing as a symbiont in the absence and presence of a test composition under conditions such that the cellulolytic organism grows, has metabolic function, or both, in the absence of the test composition; and (b) comparing the growth, metabolic function, or both, in the cellulolytic organism in the absence and presence of the test composition; wherein if the growth, metabolic function, or both, in the cellulolytic organism is less in the presence of the test composition than in the absence of the test composition, the test composition is a composition for inhibiting growth, metabolic function, or both, of the cellulolytic organism. The cellulolytic organism capable of existing as a symbiont can be an isolate of a species occurring as a symbiont. The cellulolytic organism can be a prokaryote or eukaryote. The natural host organism can be in the animal kingdom, that is metazoan, including but not limited to mollusca and arthropoda. In one aspect the cellulolytic organism is an intracellular symbiont. In another aspect the cellulolytic organism is an extracellular symbiont.

In a preferred aspect, the invention is directed to a composition identified by one or more of the methods of the invention. In a more preferred aspect, the composition does not consist essentially of a copper-containing compound, a chromium-containing compound, an arsenic-containing compound, creosote, or combinations thereof. In a more preferred aspect, the invention is directed to a method of wood preservation comprising treating the wood with the composition.

In one aspect, the invention is directed to a composition comprising an aqueous extract of a wood wherein the extract is capable of inhibiting the growth, metabolic function, or both, of a cellulolytic organism. In one embodiment, the cellulolytic organism is capable of existing as a symbiont. In a preferred embodiment, the symbiont is a shipworm symbiont.

DETAILED DESCRIPTION

In one aspect, the invention is directed to a method for identifying a composition that can be used to limit or prevent shipworm damage. The method advantageously uses *Teredinibacter*, and in one embodiment uses any species of *Teredinibacter* isolated from *B. setacea*. Any cellulolytic organism can be used that is capable of existing as a symbiont with a host organism, however, may be used in the present inventive methods. *Teredinibacter* may be grown from a single colony and can be selected for desirable traits. In the alternative, a mixed population of *Teredinibacter* may be used for the assay. Moreover, other species or a combination of species are suitable as long as they are in a symbiotic relationship with a wood-degrading or wood damaging host organism.

Variants of the symbiont, including variants selected for expression or lack of expression of genetic traits, are suitable for use in the invention. Genetically engineered variants of the symbiont are also suitable. Such variants can be obtained by standard methods.

The incubation of the symbiont can be at, below, or above ambient, including, but not limited to from about 4° C. to about 40° C. In one embodiment the incubation temperature is between about 16° C. and about 32° C. In one embodiment, the incubation temperature is between about 24° C. and about 28° C. The incubation can be performed in liquid suspension, in semi-solid suspension, or on plates. In one aspect, the incubation of the symbiont is carried out on agar plates. The determination of inhibition can be by any method known in the art, including detecting a zone of inhibition, a zone of effect, plaque formation, plaque inhibition, growth, inhibition of growth, catabolism of substrates, generation of metabolic products, and inhibition of generation of metabolic products. The inhibition can be total or partial. In one embodiment the incubation is at 26° C. for two days using a lawn of symbiont and detecting inhibition by bacterial lysis.

The *Teredinibacter*, or other symbiont, may be propagated by means standard in the art. For example, *Teredinibacter* may be cultured in aerobic or microanaerobic conditions. *Teredinibacter* may be grown in natural or synthetic seawater, with a cellulose carbon source, and an inorganic nitrogen source such as ammonium chloride. See, e.g. Waterbury et al., supra; Sipe et al., *Bacterial symbiont transmission in the wood-boring shipworm Bankia setacea(Bivalvia: Teredinidae)*, 66 Applied and Environmental Microbiology 1685 (2000).

*Teredinibacter* are advantageously grown for the assay on agar plates, but may be grown in any method known in the art including in suspension and in semi-solid suspension.

The test composition can be administered to the symbiont in any of a number of ways, including as a liquid extract, as a dry powder, as a solution, as a suspension, and dried on an inert support. A range of total amount of test composition is advantageously evaluated. The concentration effective for inhibition of the symbiont can be determined from measurements at a plurality of concentrations.

Any of a number of means known in the art can be used for detecting inhibition of a symbiont, including *Teredinibacter*, by a test compound. Effective methods include detecting a zone of inhibition surrounding a discrete site of administration of a composition, which can be done on a lawn of bacteria. In other methods the number of bacterial colonies, or plates, formed in response to the administration of the composition can be quantitated. Moreover, the rate of growth and the attenuation or inhibition of growth by administration of the test composition can be detected by turbidometric methods. An assay based on metabolism of substrates can be used to detect changes in growth rate. For example, cellulose derivatized with a marker dye or fluorescent dye can be used as a substrate. Among these dyes can be ostazin brilliant red h-3b. Release of the dye from insoluble cellulose can indicate metabolism of the cellulose. The assay can also be based on production of a metabolic product or inhibition of production of a metabolic product. For example, the production of sugars and/or glucose from digestion of cellulose can be detected. The invention is not limited to the exemplary methods provided.

A composition can be selected that produces a partial inhibition of the growth or metabolic activity of the symbiont, or total inhibition of the symbiont. In one embodiment, compositions are effective at inhibiting the symbiont at below ambient temperatures, as may be found in marine environments. In another embodiment, compositions inhibit the symbiont at temperatures typically found in estuarine environments. In yet another embodiment, the compositions inhibit the symbiont at temperatures found on land.

In one aspect, the invention is a method of wood preservation comprising treating the wood with at least one of the compositions of the invention. The wood can be surface-treated or pressure-treated by methods standard in the art or by methods readily adaptable by one of skill in the art. The wood can be treated for about a few minutes, about a few hours, or about a few days. The composition can be used at any concentration, including, but not limited to about 0.01 g/l, about 1.0 g/l, and about 100 g/l. In one embodiment, the wood is treated for two days at two atmospheres with 0.1 g/l of solids in water.

The invention also comprises a method of wood preservation comprising treating the wood with the above composition by trapping the composition, in whole or in part, in the wood by physical or chemical means. Physical means include treating the wood at elevated temperature, elevated pressure, or both. Chemical means include using co-fixatives, including, but not limited to formaldehyde and carbodiimide, and adjusting the ionic strength, pH, or both. The composition can be brominated, chlorinated, methylated, or acetylated before or after treating the wood. Use of a composition treated to introduce reactive substituents is also contemplated. The reactive substituents can be any known in the art, including, but not limited to carbene or nitrene-generating substitutents.

In one aspect, the invention comprises a composition comprising an extract of a plant, a part of a plant, plant cells, or a wood capable of inhibiting the growth of a cellulolytic symbiont. The symbiont can be a bacterium, including, but not limited to *Teredinibacter*. In one particular embodiment, the composition comprises an extract of heartwood. In another embodiment, the composition comprises an aqueous extract of heartwood.

The plant or wood can be any plants or woods having symbiont-inhibiting properties, including, but not limited to Douglas fir, ebony, jarrah, koa, lignum vitae, narra, Osage orange, paduccah, purpleheart, red alder, red oak, teak, verawood, western red cedar, or combinations thereof. Plant cells grown in cell culture are also suitable as sources of components of the composition. In one embodiment, cells of symbiont-inhibiting trees are propagated in cell culture. The cells can be leaf, stem, or root cells. The cells can be propagated by any means known in the art.

The composition can comprise an aqueous extract. The water component can be tap, distilled, or deionized water. The water can be potable, but non-potable water is also useful in the invention. The extractive medium can include salts or minerals and be of any ionic strength. The salts can be volatile salts such as ammonium bicarbonate or non-volatile salts such as sodium chloride. A variety of pH values of the extractive medium are useful in the invention, from about pH 1 to about pH 14. In one embodiment the pH of the extractive medium is between about pH 3 and pH 10. In other embodiments, the pH is between about 3 and pH about 7, or between about 7 and about 10. Any suitable acid or base can be used to adjust the medium. Moreover, the extractive medium can have water-miscible organic solvents including alcohols or ketones, used without or with water.

In one aspect, the invention is directed to a method for identifying inhibitors of a cellulolytic organism comprising the steps of: (a) incubating a cellulolytic organism capable of existing as a symbiont in the absence and presence of a test composition under conditions such that the cellulolytic organism exhibits at least one of growth and metabolic function in the absence of the test composition; and (b) comparing at least one of the growth and the metabolic function of the cellulolytic organism in the absence and presence of the test composition; wherein if at least one of the growth and metabolic function in the cellulolytic organism is less in the presence of the test composition than in the absence of the test composition, the test composition comprises an inhibitor of the cellulolytic organism. In the method, a test composition is incubated with the cellulolytic organism. The incubation may be at any convenient temperature including below ambient temperatures, at about ambient temperatures, or above ambient temperatures. In one embodiment a temperature of about 4° C. to about 40° C. is used. In another embodiment a temperature of between about 16° C. and 36° C. is used. In one embodiment a temperature of about 28° C. is used. A suitable temperature is easily selected by one of skill in the art with a view toward both propagation and detection of inhibition of an organism capable of existing as a symbiont. Inhibition of either growth or metabolism of the symbiont organism can be determined in any of a number of ways. The inhibition can be determined by detecting a zone of an inhibition, a zone of effect, plaque formation, plaque inhibition, growth of the organism, inhibition of growth of the organism, catabolism of substrates, generations of metabolic products, and inhibition of generation of metabolic products. A composition can be selected that provides partial inhibition of the growth or metabolism of the organism, or provides total inhibition of the growth or metabolism of the organism. The identified composition is useful as a candidate for the inhibition of organisms capable of existing as a symbiont. The method is suitable for the case in which the organism is capable of existing as a shipworm symbiont. Moreover the method is suitable for the situation where the organism is a *Teredinibacter*. The method is also suitable for the case in which the organism is capable existing as a termite or silverfish symbiont.

Compositions identified by the above assay are suitable for the invention. In one embodiment of the invention the compositions do not include compositions consisting essentially of a copper-containing compound or a chromium-containing compound, such as cupric chromate, an arsenic-containing compound such as cupric arsenic, creosote, or combinations thereof.

The invention is also directed to a method of wood preservation comprising treating wood with a composition known to inhibit a cellulolytic organism. The treated wood can be used for ship building, for building in an estuarine or marine environment; for building piers, for preparing docks, or any other suitable use. The wood can be treated by surface treatment such as by application of the composition of the invention in a paint or spray or stain. The wood to be preserved can in the alternative be treated under high pressure or elevated temperature to induce the permeation of the composition of the invention into the fiber of the wood.

The compositions of the invention include an extract of a plant, a part of a plant, or plant cells, capable of inhibiting the growth of a cellulolytic symbiont, and also include any synthetic analogs of the extracts. The compositions of the invention may by synthesized by means standard in the art. Moreover, combinations of ingredients are within the purview of the invention.

The invention is also directed to a method for the inhibition of wood degradation by shipworms comprising contacting wood with an inhibitor of a bacterial symbiont of *Bankia setacea*, with a proviso that the composition does not consist essentially of a copper-containing compound, a chromium-containing compound, an arsenic-containing compound, creosote, or combinations thereof. Copper, chromium and arsenic-containing compounds are commonly used in the wood preserving industry, for example as chromate copper arsenic (CCA), which are thought to be major sources of environmental degradation from the leaching of toxic heavy metals and poisons.

The use of the singular form in this description is meant to include the plural. Thus, for example, "cellulolytic organism" includes a population of the organism, and multiple strains or species, unless the text refers to a single organism. By "symbiont" is meant an organism living, or capable of living in symbiosis with a host organism. A symbiont is not a fungus as used in this application. The term cellulolytic organism includes organisms that can survive using cellulose as the primary or only carbon nutrient source. *Teredinibacter* is an example of a cellulolytic organism. Host organisms shelter cellulolytic organisms in a process that provides metabolic energy from cellulose for the host.

EXAMPLES

Example 1

Heartwood samples of fourteen wood species (Table 1) are ground to pass a 40 mesh per inch screen. The sawdust samples are oven-dried at 104° C. before undergoing the following sequential extraction process.

TABLE 1

Selected wood species used in bioassays against *Aspergillus niger* and a bacterial symbiont of *B. setacea*.

| Common Name | Latin Name |
| --- | --- |
| Teak | *Tectona grandis* L. f. |
| Ebony | *Diospyros ebenum* Koenig |
| Jarra | *Eucalyptus marginata* Sm. |
| Lignumvitae | *Guaiacum sanctum* L. |
| Purpleheart | *Peltogyne* spp. |
| Padauk | *Pterocarpus dalbergioides* Roxb. |
| Verawood | *Bulnesia arborea* (Jacq.) Engler |
| Koa | *Acacia koa* Gray |
| Narra | *Pterocarpus indious* Willd. |
| Red alder | *Alnus rubra* Bong. |
| Red oak | *Quercus rubra* L. |
| Douglas-fir | *Pseudotsuga menziesii* (Mirb.) Franco |
| Western redcedar | *Thuja plicata* Donn ex. D. Don |
| Osage orange | *Maclura pomifera* (Raf.) C.K. Schneid |

First, a 10 g sub-sample of oven dried sawdust from each wood species is placed into a tared beaker along with 100 ml of distilled water. The beakers are covered with aluminum foil and steamed for 20 minutes at 100° C. The slurry is then filtered under suction through Whatman #4 filter paper and the liquid extract retained for use in the bioassay described below. The residual sawdust is returned to the beaker, oven-dried for 24 hours at 104° C. and weighed. Next, one hundred ml of hot methanol (60° C.) is added to each of the sawdust samples. After 60 minutes the resulting extract is collected by filtration as described above and retained. The sawdust is again returned to the beaker, dried for 24 hours at 104° C. and weighed. Finally, 100 ml of toluene is added to each of the sawdust samples, the beakers are covered with Parafilm and the samples are allowed to steep for 60 minutes. The extract is collected and retained. The sawdust is again returned to the beaker, dried, and weighed.

A series of paper discs with increasing levels of extractives are prepared by adding either one, two, three or four 10 µl aliquots of extract to 6 mm diameter BBL Blank Taxo Test Discs (Becton Dickinson and Company, Cockeysville, Md., 21030, U.S.A. ). The discs are allowed to dry between additions. Control discs are treated similarly with distilled water, methanol and toluene. An additional series of blank discs are treated with single 10 µl aliquots of 1, 5, 10, 25, 50 and 100 ppm solutions of the antibiotic streptomycin sulfate to serve as positive controls for inhibition of the symbiont.

Toxicity of the treated paper discs is evaluated in two bioassays. In the first, the discs are placed on the surface of potato dextrose agar (PDA) piates seeded with spores and hyphal fragments of the common wood inhabiting mold *Aspergillus niger* Van Tiegh according to the procedures described in the American Society for Testing Materials Standard D 5583-94 (ASTM, 1999). This fungus is commonly used for detecting and quantifying the presence of preservatives in wood and is very sensitive to low levels of toxicants, particularly phenolic compounds. In the second bioassay the treated discs are evaluated against the shipworm symbiont seeded on the surface of plates containing a specialized cellulose medium (Table 2). The plates are incubated at 28° C. until the fungal spores becomes pigmented or the bacterium completely covers the surface of the plate. At that time, the maximum zone of inhibition (ZOI) and maximum zone of effect (ZOE) are measured around each disc to the nearest mm, and the diameter of each disc is subtracted.

TABLE 2

Ingredients of a specialized cellulose medium used for culturing a bacterial symbiont of *B. setacea*.

| Ingredient | Quantity (per liter) |
| --- | --- |
| Synthetic sea water[a] | 750.0 ml |
| Distilled water | 249.0 ml |
| HEPES buffer | 5.2 g |
| Sigmacell 101 cellulose | 5.0 g |
| Agar | 9.0 g |
| $K_2HPO_4$ | 116.7 mg |
| $Na_2CO_3$ | 99.6 mg |
| $Na_2MoO_4 2H_2O$ | 27.2 mg |
| EDTA disodium salt | 4.8 mg |
| Ferric ammonium citrate | 30.0 mg |
| $NH_4Cl$ | 26.8 mg |
| Trace metal mix A-5 + Co[b] | 1.0 ml |
| John Waterbury's VA vitamin mix[c] | 200 µl |

[a]Composed of 24.0 g NaCl, 7.0 g $MgSO_4$—$7H_2O$, 5.3 g $MgCl_2$—$6H_2O$, 0.7 g KCl, 0.1 g $CaCl_2$ in 1 liter distilled water; pH adjusted to 7.5. In: Atlas, R.M. 1993. Handbook of Microbiological Media. CRC Press, Inc., 2000 Corporate Blvd., N.W., Boca Raton, Florida, 33431. U.S.A.
[b]Rippka, R., J. Deruelles, J.B. Waterbury, M. Herdman, and R. Y. Stanier 1979. Generic assignments, strain histories, and properties of pure cultures of cyanobacteria, J. Gen. Microbiol. 111:1-61.
[c]Composed of 10 mg nicotinic acid (niacin), 0.1 mg folic acid (Pteroylglutamic acid), 20 mg d-pantothenic acid, 0.4 mg p-aminobenzoic acid (PABA), 10 mg pyridoxine hydrochloride (Vitamin B6), 0.1 mg d-biotin (Vitamin H), 0.1 mg cyanocobalamin (Vitamin B12), 200 mg Thiamin hydrochloride and 100 mg myo-Inositol in 100 ml sterile distilled water.

A fungus, *Aspergillus niger*, was used as a control. Water and methanol extracts have little effect on the growth of *Aspergillus niger*, while toluene extracts consistently produce a zone of effect that is related, in whole or in part, to a residual solvent effect. While the filter discs are thoroughly aerated prior to fungal exposure, some of the solvent remains. Extracts of some wood species produce larger zones of effect including Douglas-fir, ebony, jarrah, osage orange, purpleheart, red alder, and red oak. A number of these species are highly durable. Red oak and red alder, however, produce zones of effect. Both of these species latter have little natural resistance to microbial degradation and are normally rapidly colonized by mold and stain fungi. Thus, these results indicate that the toluene extracts are not appropriate for assessing sensitivity of the test fungus to wood components.

The results with a bacterial symbiont *B. setacea* show inhibition of symbiont growth. Aqueous extracts from the various woods produce measurable zones of effect in nearly all instances. Zones of inhibition ranged from 0.2 to 40.3 mm depending upon the extract and wood species. Water extracts applied a single time to the filter paper produce zones of inhibition (ZOI) greater than 1 mm when extracts are derived from Douglas-fir, ebony, jarrah, koa, narra, osage orange, paduccah, red oak, and western redcedar. The greatest ZOI's are found with jarrah, koa, red oak, and western redcedar. The ability of red oak to inhibit the symbiont may be contrasted with the lack of durability exhibited by this species. The effect may reflect tannin extraction, which might precipitate bacterial proteins in the membrane, and thereby inhibit microbial growth. This latter effect would be expected to be temporary in nature, because tannins leach relatively rapidly from wood when immersed in water. The lack of effect by osage orange at the lowest treatment level is also interesting since this wood is reported to contain large quantities of a number of highly toxic extractives. Multiple applications of most of the water extracts of heartwoods, except lignum vitae and verawood, tended to increase the zones of inhibition for the symbiont. Lignum vitae has a reputation for durability and the absence of a substantial effect against the symbiont implies that other mechanisms must account for its durability.

Zones of inhibition in cultures exposed to methanol extracts of the various wood species tend to follow trends that are similar to those found with the water extracts. ZOI's greater than 1 mm are found with single applications of 12 of the 14 species tested. The largest ZOI's are found with jarrah, koa, red oak, and western redcedar. The three species (jarrah, koa, and western redcedar) exhibit some resistance to marine borer attack and symbiont inhibition may play a role in that inhibition. Interestingly, some of these species, notably western redcedar tend to inhibit shipworm damage well for short periods of time, then fail rapidly, a characteristic suggestive of loss of toxic extractives by leaching over time. Toluene extracts produced no consistent zones of inhibition for the wood species tested, suggesting that any effective extracts had already been removed during water and methanol extraction, or alternatively, that the inhibitors are not soluble in toluene.

The symbiont is vertically acquired in the shipworm *Bankia setacea*, such that the larvae appear to carry the symbiont to the wood. Sipe et al., supra. The initial settlement of the shipworms on wood, colonization, and growth dependent on digestion of cellulose are independent processes subject to intervention to disrupt the shipworm cycle.

Compounds that affect the symbiont may differently affect the ability of the marine borer to digest cellulose, to establish new settlements, and to colonize. Previous reports have established that shipworms are able to move from an untreated wood member through a preservative treated member and into another. Preventing settlement, halting establishment, and depleting nutrients are each critical aspects of marine borer control. The tested compositions of wood extracts are clearly effective at inhibiting the symbiont growth and metabolism. Combination of methods to limit settlement or establishment of shipworms with the methods and compositions of the invention can result in further enhancement of protection of wood in marine or estuarine environments.

Example 2

Acetylation of extracts: An about 50 μg portion (dry weight) of an extract having inhibitory properties is stirred in a sealed glass vial with 100 μL of acetic anhydride (Supelco) and 100 μL of dry pyridine for 3 h. The reaction mixture is washed with saturated NaCl, then partitioned between saturated aqueous $NaHCO_3$ and ethyl acetate. The organic, that is, ethyl acetate, layer is collected and concentrated. The product of the acetylation reaction may be significantly less polar than the starting material by silica gel TLC analysis, indicating masking of hydroxyl moieties, carboxyl moieties, or both, by the acetylation reaction.

Example 3

A solution based assay: A dye-release solution-phase assay is based on the detection of cellulose-degrading activity based on specific interaction of direct dyes such as Congo red with polysaccharides. Congo Red reacts with beta-1,4-glucans causing a visible red shift (Wood, P. J., Carbohydr. Res., 85:271 (1980) and Wood, P. J., Carbohydr. Res., 94:19 (1981)). A preferred substrate for the test is carboxymethylcellulose which can be obtained from different sources such as Hercules Inc., Wilmington, Del., Type 4M6F or Sigma Chemical Company, St. Louis, Mo., Medium Viscosity. The carboxymethylcellulose is incorporated as the main, or sole, carbon source into a minimal agar medium in quantities of 0.1-1.0%. The effect of the symbiont can be screened directly on these plates. Symbiont can be pretreated with putative inhibitor or can be over laid with filter paper impregnated with putative inhibitor. Such cellulase-producing colonies are detectable after a suitable incubation time (1-3 days depending on the growth), by addition of a 0.1% aqueous solution of Congo Red. The coloration is terminated after 20 minutes by removing the dye and adding 5M NaCl solution to the plates. The technique can be adapted as a cup-plate diffusion assay for the determination of carboxymethylcellulase activity in culture filtrates.

Example 4

The effect of compositions can also be detected in an endoglucanase assay, as follows. The endoglucanase activity is determined as the decrease in the viscosity of a solution of carboxymethyl cellulose after incubation of symbiont with test compositions under the following conditions: A substrate solution is prepared, containing 35 g/l carboxymethylcellulose in culture medium. The sample to be analyzed is dissolved or dispersed in the same medium. Then 10 ml substrate solution and 0.5 ml symbiont sample are incubated at 32° C. for 24 hrs in the absence or presence of 0.5 ml inhibitor. Then the sample is transferred to a viscosimeter (e.g. Haake VT 181, NV sensor, 181 rpm), at a controlled temperature of 32° C. Viscosity readings are taken at several intervals thereafter. The concentration of inhibitor product that prevents a decrease in viscosity by one half under these conditions is defined as the 50% effective concentration.

All of the references cited herein are incorporated by reference in their entirety, for all purposes.

Although the foregoing invention has been described in some detail for purposes of clarity of understanding, it will be apparent that certain changes and modifications may be practiced within the scope of the invention. It should be noted that there may be alternative ways of implementing both the methods and compositions of the present invention. Accordingly, the present embodiments are to be considered as illustrative and not restrictive, and the invention is not to be limited to the details given herein.

What we claim is:

1. A method for identifying a composition for limiting shipworm damage comprising the steps of:
   (a) incubating a shipworm symbiont in the absence and presence of a test composition under conditions such that the shipworm symbiont grows, has metabolic function, or both, in the absence of the test composition; and (b) comparing the growth, metabolic function, or both, in shipworm symbionts in the absence and presence of the test composition;

wherein if the growth, metabolic function, or both, in shipworm symbionts is less in the presence of the test composition than in the absence of the test composition, the test composition is a composition for limiting shipworm damage.

2. The method of claim 1 wherein the symbiont is a *Teredinibacter*.

3. The method of claim 1, wherein the test composition is a wood extract.

4. The method of claim 3, wherein the wood extract is an aqueous extract from a wood selected from the group consisting of Douglas-fir, ebony jarrah, koa, lignum vitae, narra, Osage orange, paduccah, purpleheart, red alder, red oak, teak, verawood, and western red cedar.

5. The method of claim 4, wherein the wood is selected from the group consisting of jarra, koa, red oak and western red cedar.

* * * * *